United States Patent [19]

Meyer et al.

[11] 4,004,014
[45] Jan. 18, 1977

[54] 2-AMINO-6-DIALKYLAMINODIHY-DROPYRIDINES, THEIR PRODUCTION, PHARMACEUTICAL COMPOSITIONS AND METHODS OF USE THEREOF

[75] Inventors: Horst Meyer; Friedrich Bossert, both of Wuppertal; Wulf Vater, Opladen; Kurt Stoepel, Wuppertal, all of Germany

[73] Assignee: Bayer Aktiengesellschaft, Germany

[22] Filed: Jan. 29, 1975

[21] Appl. No.: 545,202

[30] Foreign Application Priority Data

Feb. 9, 1974 Germany ............................ 2406198

[52] U.S. Cl. ........................ 424/266; 260/295.5 R
[51] Int. Cl.² ............ A61K 31/455; C07D 211/00; C07D 401/00
[58] Field of Search .............. 260/295.5 R; 424/266

[56] References Cited
UNITED STATES PATENTS 3,887,558  6/1975  Meyer et al. ............... 260/295.5 R

OTHER PUBLICATIONS

David et al., Chem. Abst., vol. 70 (1969), p. 47393R.

*Primary Examiner*—Sam Rosen

[57] ABSTRACT

2-Amino-6-dialkylaminodihydropyridines exist in tautomeric form and are represented by the formulae

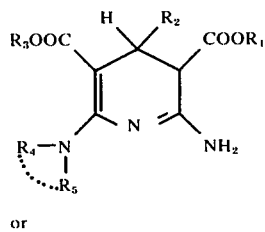

Ia or

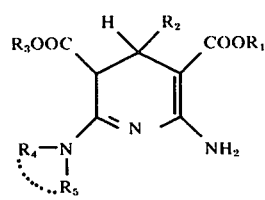

Ib wherein $R_1$ and $R_3$ are the same or different and each is straight, branched or cyclic alkyl, alkenyl or alkynyl or said alkyl, alkenyl or alkynyl interrupted by 1 or 2 oxygen atoms;

$R_2$ is a saturated, partially unsaturated or unsaturated straight, branched or cyclic hydrocarbon; aryl unsubstituted or substituted by 1, 2 or 3 of the same or different substituents selected from the group consisting of alkyl, alkoxy, azido, halo, cyano, nitro, trifluoromethyl, carbalkoxy and $SO_n$-alkyl wherein $n$ is 0, 1 or 2; naphthyl; quinolyl; isoquinolyl; pyridyl; pyrimidyl; thenyl; or furyl; and $R_4$ and $R_5$ are each lower alkyl; benzyl; or, together with the nitrogen atom to which they are attached, a 4- to 7-membered ring. These compounds are useful for their coronary-vessel-dilating effect, their antihypertensive effect, their anti-fibrillation effect, their vascular-spasmolytic effect and their muscular-spasmolytic effect.

13 Claims, No Drawings

2-AMINO-6-DIALKYLAMINODIHYDROPYRIDINES, THEIR PRODUCTION, PHARMACEUTICAL COMPOSITIONS AND METHODS OF USE THEREOF

The present invention is concerned with 2-amino-6-dialkylaminodihydropyridines, a process for their production, pharmaceutical compositions utilizing said compounds as the active agents, and methods of use involving administration of said compounds.

It is known in the art that the reaction of aromatic aldehydes with a twofold molar amount of 3-aminocrotonic acid esters leads to 2,6-dialkyl-1,4-dihydropyridines [Cook, Heilbron and Steger, J. Chem. Soc., 1943, 413 (London)]. It is also known that the condensation of aromatic aldehydes with a twofold molar amount of amidinoacetic acid esters leads to 2,6-diaminodihydropyridines (German DOS 2,210,687).

More particularly, the present invention is concerned with 2-amino-6-dialkylaminodihydropyridines which may exist in the tautomeric general formulae below:

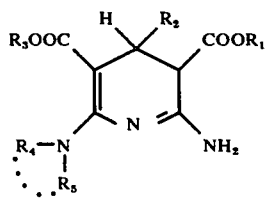

Ia or

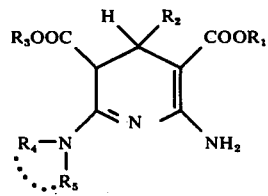

Ib wherein $R_1$ and $R_3$ are the same or different and each is straight or branched chain alkyl, preferably lower alkyl; cycloalkyl, preferably of 4 to 7 carbon atoms; straight or branched chain alkenyl, preferably lower alkenyl; cycloalkenyl, preferably of 4 to 7 carbon atoms; straight or branched chain alkynyl, preferably lower alkynyl; cycloalkynyl, preferably of 4 to 7 carbon atoms; or said alkyl, alkenyl or alkynyl interrupted by 1 or 2 oxygen atoms;

$R_2$ is a saturated, partially unsaturated or unsaturated, straight, branched or cyclic hydrocarbon, preferably straight or branched chain lower alkyl; straight or branched chain lower alkenyl; straight or branched chain lower alkynyl; cycloalkyl of 4 to 7 carbon atoms; cycloalkenyl of 4 to 7 carbon atoms; or cycloalkynyl of 4 to 7 carbon atoms; aryl unsubstituted or substituted by 1, 2 or 3 of the same or different substituents selected from the group consisting of alkyl, especially lower alkyl, alkoxy, especially lower alkoxy, azido, halo, cyano, nitro, trifluoromethyl, carbalkoxy, especially carb(lower alkoxy), and $SO_n$-alkyl, especially lower alkyl, wherein $n$ is 0, 1 or 2; naphthyl; quinolyl; isoquinolyl; pyridyl; pyrimidyl; thenyl; or furyl; and $R_4$ and $R_5$ are each alkyl, especially lower alkyl; benzyl; or, together with the nitrogen atom to which they are attached, form a 4- to 7-membered ring system.

In the tautomeric formulae, I$a$ represents the 3,4-dihydro structure and I$b$ represents the 4,5-dihydro structure.

The compounds of the present invention may be prepared by:

a. reacting an aldehyde of the formula $$R_2CHO \qquad (II),$$

wherein $R_2$ is as above defined, with an N,N-dialkyl-3,3-diaminoacrylic acid ester of the formula

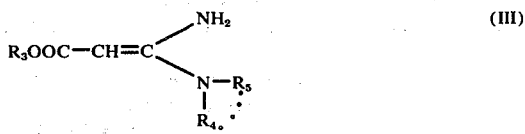

(III)

wherein $R_3$, $R_4$ and $R_5$ are as above defined, in an inert organic solvent; or b. reacting an ylidene cyanoacetic acid ester of the formula

(IV), wherein $R_1$ and $R_2$ are as above defined, with an N,N-dialkyl-3,3-diaminoacrylic acid ester of the formula (III) above wherein $R_3$, $R_4$ and $R_5$ are as above defined, in the presence of an alkali metal alcoholate and an inert organic solvent.

The compounds of the present invention are particularly useful for their coronary-vessel-dilating effect and their antihypertensive effect.

It is very surprising that in the process according to the present invention the new 2-amino-6-dialkylaminodihydropyridines of the formula (I) are produced in such good yields and with such high purity. In view of the prior art it could have been expected in process variant (a) that 2,6-bis-dialkylamino-1,4-dihydropyridines would be formed in accordance with the following reaction scheme:

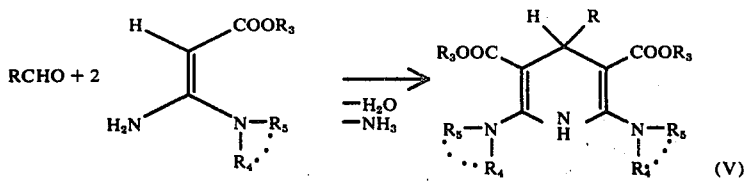

(V)

since, according to the literature (Cook, Heilbron and Steger, J. Chem. Soc., 1943, 413 (London)), the reaction of aldehydes with 3-aminocrotonic acid esters leads, as mentioned above, to 2,6-dialkyl-1,4-dihydropyridines.

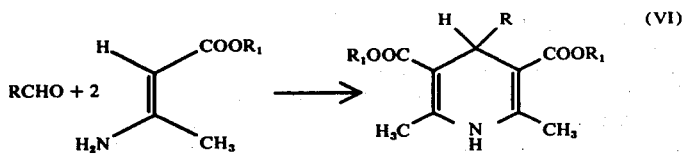

However, the formation of the 2,6-bis-dialkylamino-1,4-dihydropyridines of the formula (V) has not been observed in the process according to the present invention.

An important advantage of the process, in addition to the good yields, is that it can be carried out as a one-step process with little technical effort and highly economically.

If, for example, 3-nitrobenzaldehyde and N,N-dimethyl-3,3-diaminoacrylic acid ethyl ester are used as starting materials, the course of the reaction in process variant (a) can be represented by the following scheme:

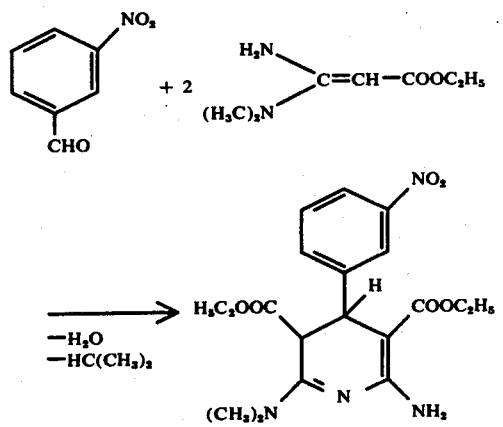

If, for example, 2-nitrobenzylidenecyanoacetic acid ethyl ester and 3-pyrrolidino-3-aminoacrylic acid isopropyl ester are used as starting materials, the course of the reaction in process variant (b) can be represented by the following scheme:

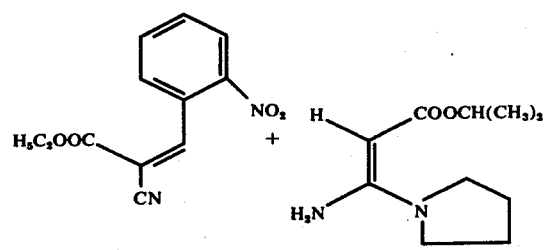

(VI)

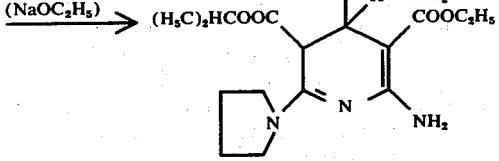

According to one embodiment of the present invention $R_1$ and $R_3$ are the same or different and each is straight or branched chain alkyl of 1 to 6 carbon atoms or straight or branched chain alkynyl of 2 to 6 carbon atoms;

$R_2$ is straight or branched chain alkyl of 1 to 6 carbon atoms; straight or branched chain alkynyl of 2 to 6 carbon atoms; cycloalkyl of 4 to 6 carbon atoms; cycloalkynyl of 4 to 6 carbon atoms; phenyl unsubstituted or substituted by 1 or 2 of the same or different substituents selected from the group consisting of alkyl of 1 to 4 carbon atoms, alkoxy of 1 to 4 carbon atoms, halo, nitro, cyano, trifluoromethyl, carb(alkoxy) of 1 to 4 carbon atoms in the alkoxy moiety and $SO_n$-alkyl of 1 to 4 carbon atoms in the alkyl moiety and wherein $n$ is 0 or 2; naphthyl; pyridyl; thenyl; or furyl; and $R_4$ and $R_5$ are straight or branched chain alkyl of 1 to 4 carbon atoms; benzyl; or, together with the nitrogen atom to which they are attached, a 5- to 7-membered ring.

According to another embodiment of the present invention $R_1$ and $R_3$ are the same or different and each is straight or branched chain alkyl of 1 to 4 carbon atoms or straight or branched chain alkynyl of 2 to 4 carbon atoms; and $R_2$ is alkyl of 1 or 2 carbon atoms; phenyl unsubstituted or substituted by 1 or 2 of the same or different substituents selected from the group consisting of alkyl of 1 or 2 carbon atoms, alkoxy of 1 or 2 carbon atoms, chloro, bromo, nitro, cyano, trifluoromethyl, carbalkoxy of 1 or 2 carbon atoms and $SO_n$-alkyl of 1 or 2 carbon atoms wherein $n$ is 0 or 2; naphthyl; pyridyl; thenyl; or furyl.

According to another embodiment of the present invention $R_1$ is alkyl of 1 or 2 carbon atoms;

$R_2$ is phenyl unsubstituted or substituted by nitro; or pyridyl;

$R_3$ is alkyl of 1 or 2 carbon atoms; and $R_4$ and $R_5$ are each alkyl of 1 or 2 carbon atoms; or, together with the nitrogen atoms to which they are attached, a 5- or 6-membered ring wherein the nitrogen atom is the only heteroatom.

According to another embodiment of the present invention
$R_1$ is ethyl;
$R_2$ is phenyl; nitrophenyl; or pyridyl;
$R_3$ is ethyl; and
$R_4$ and $R_5$ are each methyl; or, together with the nitrogen atom to which they are attached, a pyrrolidino or piperidino ring.

The aldehydes of formula (II) are either per se known or can be prepared according to techniques per se known. (See, for example, E. Mosettig, Org. Reactions, VIII, 218 et seq. (1954).)

The following aldehydes are representative of those which can be used according to the present invention: acetaldehyde, propionaldehyde, isobutyraldehyde, cyclopentaldehyde, cyclohexanaldehyde, acrolein, 3-cyclohexanaldehyde, benzaldehyde, 2-, 3- or 4-methylbenzaldehyde, 2- 3- or 4-methoxybenzaldehyde, 3,4,5-trimethoxybenzaldehyde, 2-isopropoxybenzaldehyde, 2-, 3- or 4-chloro-, bromo- or fluorobenzaldehyde, 2,4- or 2,6-dichlorobenzaldehyde, 2,4- or 2,3-dimethylbenzaldehyde, 2-, 3- or 4-nitrobenzaldehyde, 2,6- or 3,5-dinitrobenzaldehyde, 2-nitro-6-bromobenzaldehyde, 2-nitro-3-methoxy-6-chlorobenzaldehyde, 2-nitro-4-chloro-benzaldehyde, 2-nitro-4-methoxybenzaldehyde, 2-, 3- or 4-trifluoromethylbenzaldehyde, benzaldehyde-2-carboxylic acid ethyl ester, benzaldehyde-3-carboxylic acid methyl ester, 2-, 3- or 4-azidobenzaldehyde, $\alpha,\beta$- or $\gamma$-pyridinaldehyde, 6-methylpyridin-2-aldehyde, pyrimidin-5-aldehyde, 4,6-dimethoxypyrimidin-5-aldehyde, 2-, 3- or 4-cyanobenzaldehyde, 2-methylsulphonylbenzaldehyde, 1- or 2-naphthaldehyde, 4-methyl-1-naphthaldehyde, quinolin-2-, 3-, 4-, 5-, 6-, 7- or 8-aldehyde, isoquinolin-2-, 3- or 4-aldehyde, furan-2-aldehyde and thiophen-2-aldehyde.

The N,N-dialkyl-3,3-diaminoacrylic acid esters of the formula (III) used as starting materials are not previously known but can be prepared by reaction of cyanoacetic ester imino-ethers of the formula (VII) with amines of the formula (VIII) or their salts in accordance with the following reaction scheme:

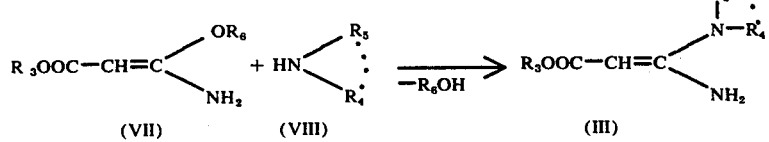

(VII)     (VIII)     (III)

The imino-ethers of the cyanoacetic esters (VII) are per se known or can be prepared according to techniques per se know. (See, for example, A. C. Cope, J.A.C.S., 67, 1017 (1945).)

The following N,N-dialkyl-3,3-diaminoacrylic acid esters of the formula (II) are representative of those which can be used according to the present invention:

N,N-3-dimethylamino-3-aminoacrylic acid methyl ester, N,N-3-dimethylamino-3-aminoacrylic acid ethyl ester, N,N-3-dimethylamino-3-aminoacrylic acid butyl ester, N,N-3-ethylmethylamino-3-aminoacrylic acid ethyl ester, N,N-3-methylisopropylamino-3-aminoacrylic acid methyl ester, 3-N-pyrrolidino-3-aminoacrylic acid ethyl ester, 3-N-pyrrolidino-3-aminoacrylic acid propyl ester, 3-N-pyrrolidino-3-aminoacrylic acid isopropyl ester, 3-N-piperidino-3-aminoacrylic acid ethyl ester and 3-N-perhydroazepino-3-aminoacrylic acid ethyl ester.

The ylidenecyanoacetic acid derivatives which can be used according to the present invention are either per se known or can be prepared according to techniques per se known. (See, for example, M. S. Newman and H. R. Flanagan, J. Org. Chem. 23, 797 (1958).)

The following ylidene cyanoacetic acid derivatives are representative of those which can be used according to the present invention: benzylidenecyanoacetic acid methyl ester, benzylidenecyanoacetic acid ethyl ester, benzylidenecyanoacetic acid propargyl ester, benzylidenecyanoacetic acid $\beta$-methoxyethyl ester, 1-naphthylidenecyanoacetic acid ethyl ester, 2-methoxybenzylidenecyanoacetic acid ethyl ester, 2-methylbenzylidenecyanoacetic acid ethyl ester, 2-nitrobenzylidenecyanoacetic acid isopropyl ester, 2-trifluoromethylbenzylidenecyanoacetic acid ethyl ester, 2-cyanobenzylidenecyanoacetic acid methyl ester, 2-chlorobenzylidenecyanoacetic acid propyl ester, 4-methylmercaptobenzylidenecyanoacetic acid ethyl ester, $\alpha$-pyridylmethylidenecyanoacetic acid ethyl ester and 2-furfurylidenecyanoacetic acid ethyl ester.

The N,N-dialkyl-3,3-diaminoacrylic acid esters (III) can be employed either in the free form or in the form of a salt (for example a hydrohalide). They may be liberated from the salts in situ by means of a basic agent (for example an alkali metal alcoholate).

All inert organic solvents can be used as diluents in the process of the invention. Preferred solvents include alcohols, such as methanol, ethanol and propanol; ethers, such as dioxan and diethyl ether; glacial acetic acid; pyridine; dimethylformamide; dimethylsulphoxide; and acetonitrile.

The reaction temperatures can be varied over a wide range. In general, the reaction is carried out at 20° C 250° C, preferably at the boiling point of the solvent.

The reaction can be carried out under normal pressure but also under elevated pressure. In general, it is carried out under normal pressure.

In carrying out the process according to the invention preferably 2 mols of the N,N-dialkyl-3,3-diaminoacrylic acid ester (III) are employed per mol of aldehyde (II) in the case of process variant (a), while in the case of process variant (b) the compounds participating in the reaction are preferred employed in equimolar amounts.

The following pharmacological action has been demonstrated in animal experiments for the compounds of the present invention:

1. The new compounds cause, on parenteral, oral and perlingual administration, a distinct and long-lasting dilation of the coronary vessels. This effect on the coronary vessels is intensified by a simultaneous nitrite-like effect of reducing the load on the heart. They influence or modify the heart metabolism in the sense of an energy saving.

2. The compounds lower the blood pressure of normotonic and hypertonic animals and can thus be used as antihypertensive agents.

3. The excitability of the stimulus-formation and excitation-conduction system within the heart is lowered, so that an anti-fibrillation action demonstrable at therapeutic doses results.

4. The tonus of the smooth muscle of the vessels is greatly reduced under the action of the compounds. This vascular-spasmolytic action can take place in the entire vascular system or can manifest itself more or less isolated in localized vascular regions (for example, the central nervous system).

5. The compounds have strong muscular-spasmolytic effects which manifest themselves on the smooth muscles of the stomach, the intestinal tract, the urogenital tract and the respiratory system.

6. The compounds influence the cholesterol level and lipid level of the blood.

The pharmaceutical compositions of the present invention contain a major or minor amount e.g. 0.1% to 99.5%, preferably 0.5% to 90% of active ingredient as above defined in combination with a pharmaceutically acceptable, nontoxic, inert diluent or carrier, the carrier comprising one or more solid semi-solid or liquid diluent, filler and formulation adjuvant which is non-toxic, inert and pharmaceuticaly acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage will be: for intravenous administration, 0.5 mg to 1,000 mg, and preferably from 0.01 to 20 mg/kg of body weight day; for oral administration, 1.0 mg to 500 mg, and preferably 0.5 to 150 mg/kg of body weight per day. In some instances a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch, lactose, sucrose, glucose or mannitol. Sweetening, flavoring, preverva-tive, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose for i.v. administration is 0.1 to 10 mg/kg of body weight per day, and in the case of oral administration, 1 to 50 mg/kg of body weight per day.

While the routes of administration include oral, parenteral (i.e., intramuscular, intraperitoneal and intravenous), rectal, and topical, oral administration and intravenous administration are particularly preferred.

The preferred pharmaceutical compositions are therefore those in a form suitable for oral administration such as tablets and suspensions and those suitable for intravenous application such as solutions and emulsions.

Tables I and II below give representative test data showing the activity of representative compounds of the present invention.

The coronary effect of two of these compounds is exemplified in Table I:

Table I

| Compound of Example No. | Dose | Duration of action |
|---|---|---|
| 1 | 10 | 20 minutes |
| 2 | 3 | 4 hours |

The above coronary effect was determined on anaesthetized heart-catheterized mongrel dogs by measuring the rise in oxygen saturation in the coronary sinus. The dose is expressed as mg/kg body weight administered intravenously, and is the dose required to cause a distinctly recognizable rise in the oxygen saturation in the coronary sinus. The duration of action is the time taken for the oxygen saturation to return to its initial value.

The blood-pressure-lowering action of some compounds according to the invention can be seen from Table II. The dose quoted in the third column is the dose, expressed in mg/kg body weight, administered perorally, required to reduce the blood pressure of hypertensive rats by at least 15 mm Hg.

Table II

| Compound of Example No. | Toxicity in mice, mg/kg given orally | Blood pressure lowering |
|---|---|---|
| 1 | — | from 100 |
| 2 | — | from 3.1 |
| 3 | 1,000 | from 100 |

The following nonlimitative examples more particularly illustrate the present invention:

EXAMPLE 1

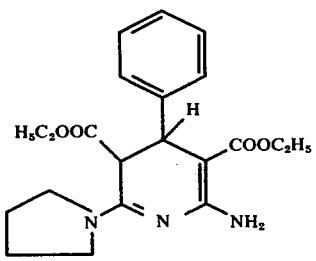

After boiling a solution of 20.1 g of benzylidenecyanoacetic acid ethyl ester, 18.4 g of 3-N-pyrrolidino-3-aminoacrylic acid ethyl ester and 1 g of sodium ethylate in 200 ml of ethanol for 4 hours, concentrating the solution and twice crystallizing the residue from ethanol, 2-amino-6-N-pyrrolidino-4-phenyl-4,5-dihydropyridine-3,5-dicarboxylic acid ethyl ester of melting point 122° C was obtained. Yield, 59% of theory.

EXAMPLE 2

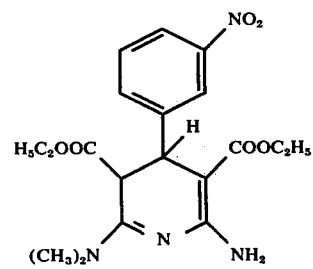

After boiling a solution of 7.5 g of 3-nitrobenzaldehyde and 15.8 g of N,N-dimethyl-3,3-diaminoacrylic acid ethyl ester in 150 ml of ethanol for 4 hours, the solution was concentrated in vacuo. On triturating the resulting oil with ether, filtering off the crystals which separated out and crystallizing these from isopropanol, the yellow-orange colored crystals of 2-amino-6-dimethylamino-4-(3'-nitrophenyl)-4,5-dihydropyridine-3,5-dicarboxylic acid diethyl ester, of melting point 149° C, were obtained. Yield, 61% of theory.

EXAMPLE 3

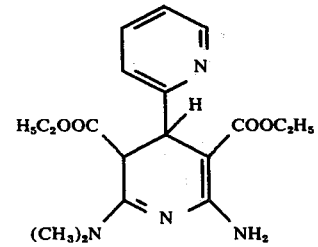

After boiling a solution of 5.4 g of pyridin-2-aldehyde and 15.8 g of N,N-dimethyl-3,3-diaminoacrylic acid diethyl ester in 150 ml of methanol for 5 hours, the solution was concentrated, the crystalline residue was triturated with ether, and the crystals were filtered off and recrystallized from isopropanol. Colorless crystals of 2-amino-6-dimethylamino-4-(2'-pyridyl)-4,5-dihydropyridine-3,5-dicarboxylic acid diethyl ester, of melting point 112° C, were obtained. Yield, 56% of theory.

EXAMPLE 4

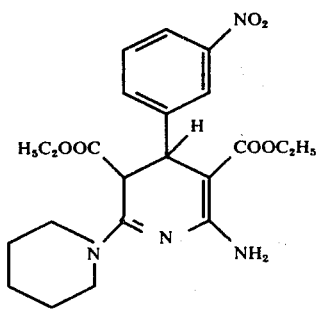

After boiling a solution of 7.5 g of 3-nitrobenzaldehyde and 19.8 g of 3-N-piperidino-3-aminoacrylic acid ethyl ester in 100 ml of ethanol for 4 hours, the solution was concentrated in vacuo and taken up in hot ethyl acetate/petroleum ether (1:1). On cooling strongly, an (orange-yellow) oil separated out, which on preparative Craig distribution gave pure 2-amino-6-N-piperidino-4-(3'-nitrophenyl)-4,5-dihydropyridine-3,5-dicarboxylic acid diethyl ester (oil). Yield, 46% of theory.

What is claimed is:

1. A compound of the tautomeric formulas:

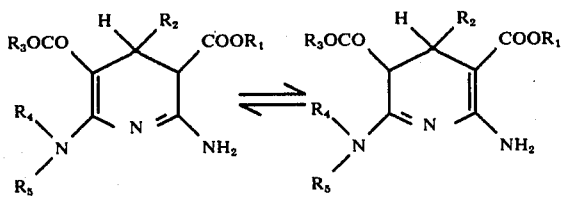

wherein each of $R_1$ and $R_3$ is alkyl of 1 to 6 carbon atoms;

$R_2$ is phenyl; phenyl substituted by methyl, methoxy, chloro, bromo, fluoro, nitro, trifluoromethyl, or azido; or pyridyl; and $R_4$ and $R_5$ when taken independently are lower alkyl or when taken together, with the nitrogen to which they are attached, pyrrolidino or piperidino.

2. The compound according to claim 1 which is 2-amino-6-pyrrolidino-4-phenyl-4,5-dihydropyridine-3,5-dicarboxylic acid diethyl ester.

3. The compound according to claim 1 which is 2-amino-6-dimethylamino-4-(3-nitrophenyl)-4,5-dihydropyridine-3,5-dicarboxylic acid diethyl ester.

4. The compound according to clam 1 which is 2-amino-6-dimethylamino-4-(pyrid-2-yl)-4,5-dihydropyridine-3,5-dicarboxylic acid diethyl ester.

5. The compound according to claim 1 which is 2-amino-6-piperidino-4-(3-nitrophenyl)-4,5-dihydropyridine-3,5-dicarboxylic acid diethyl ester.

6. A compound according to claim 1 wherein
$R_1$ is methyl or ethyl;
$R_2$ is phenyl; nitrophenyl; or pyridyl;
$R_3$ is methyl or ethyl; and
$R_4$ and $R_5$ are each methyl or ethyl; or, together with the nitrogen atoms to which they are attached, pyrrolidino or piperidino.

7. A compound according to claim 6 wherein
$R_1$ is ethyl;
$R_3$ is ethyl; and
$R_4$ and $R_5$ are each methyl; or, together with the nitrogen atom to which they are attached, pyrrolidino or piperidino.

8. The method of effecting coronary vessel dilation and reducing blood pressure in humans and other animals which comprises administering thereto an effective amount of a compound according to claim 1.

9. A pharmaceutical composition comprising a compound according to claim 1 in combination with a pharmaceutically acceptable carrier.

10. A process which comprises allowing an acrylate of the formula:

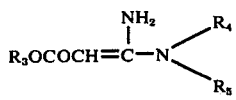

wherein $R_3$, $R_4$ and $R_5$ are as therein defined to react (a) with an aldehyde of the formula $R_2CHO$ wherein $R_2$ is as herein defined at a molar ratio of about 2:1 in an inert organic solvent to yield a compound according to claim 1 wherein $R_1$ is the same as $R_3$, or (b) with about an equimolar amount of an ylidene cyanoacetate of the formula:

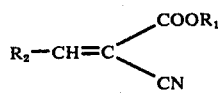

wherein $R_1$ and $R_2$ are as herein defined in an inert organic solvent and in the presence of an alkali metal alcoholate to yield a compound according to claim 1.

11. A process according to claim 10 wherein the inert organic solvent is methanol, ethanol, propanol, dioxan, diethyl ether, glacial acetic acid, pyridine, dimethylformamide, dimethylsulphoxide or acetonitrile.

12. A process according to claim 10 wherein the reaction is conducted at a temperature of from 20° to 250° C.

13. A process according to claim 10 wherein the reaction is conducted at the boiling point of the solvent.

* * * * *